United States Patent [19]

Saitou

[11] Patent Number: 4,834,070
[45] Date of Patent: May 30, 1989

[54] ENDOSCOPE WITH DEVICE FOR SHAPE RECOGNITION

[75] Inventor: Satoshi Saitou, Tochigi, Japan

[73] Assignee: Kabushiki Kaisha Toshiba, Kawasaki, Japan

[21] Appl. No.: 250,105

[22] Filed: Sep. 28, 1988

[30] Foreign Application Priority Data

Sep. 30, 1987 [JP] Japan .................. 62-243988

[51] Int. Cl.$^4$ .............................................. A61B 1/04
[52] U.S. Cl. ........................................ 128/6; 358/98
[58] Field of Search .................... 128/4, 6; 358/98

[56] References Cited

U.S. PATENT DOCUMENTS 3,703,169  11/1972  Ouchi ............................. 128/6
4,350,149  9/1982  Yamashita et al. ............ 128/6

Primary Examiner—William H. Grieb
Attorney, Agent, or Firm—Foley & Lardner, Schwartz, Jeffery, Schwaab, Mack, Blumenthal & Evans

[57] ABSTRACT

An endoscope is disclosed which incorporates an easily maneuverable device for recognizing the shapes of imaged objects. The endoscope includes device to project patterned beams on the objects, device to identify positions of spots made on the objects by the patterned beams, device to indicate the identified positions of the spots on a displayed image of the objects, device to correct errors found in the identified positions of the spots, and device to adjust the indications on the displayed image of the objects according to the corrections made.

3 Claims, 5 Drawing Sheets

X : MARKING
O : SPOT
--- : C.D. CURVE BEFORE CORRECTION
——— : C.D. CURVE AFTER CORRECTION

ENDOSCOPE WITH DEVICE FOR SHAPE RECOGNITION

BACKGROUND OF THE INVENTION

1. Field of the Invention

The present invention relates to an endoscope and, more particularly, to an endoscope with a device to facilitate recognition of shapes of imaged objects.

2. Description of the Prior Art

The recognition of shapes of imaged objects on a display can be facilitated in an endoscope by incorporating a device for projecting patterned light beams on imaged objects and measuring deviation of an imaged pattern from the original pattern due to parallax.

The patterned light beams are provided, for example, by means of laser beams through a diffraction grating. Such a device is shown in FIG. 1. A grating 1 is constructed by combining two sheets of glass-fibres, each sheet being comprised of an array of glass-fibres, such that each glass-fibre of one sheet intersects with glass-fibres of the other sheet at right angle. As shown in FIG. 1, when laser beams 2 from a laser 3 are shone on such a diffraction grating 1, patterned beams 4 emerge from the other side which when projected on a flat screen 5 exhibit a regular array of spots as a diffraction pattern.

Now, if such patterned beams 4 are projected on an irregular surface and spots on the surface are observed from a point separated from a point from which patterned beams 4 emerged, a deviation of an observed pattern from the original pattern appears, which is a phenomenon known as a parallax. This is shown in FIG. 2, where G is the point from which the patterned beams 4 emerge, A is the point of observation, Pa is a parallax distance separating G and A, and the patterned beams 4 are projected on the irregular surface of an object 6 to be imaged. Since deviations of patterns due to parallax depend on parallax distances and shapes of surfaces, by fixing a parallax distance the information on the shape of an object can be obtained from the observation of a deviation. This can be implemented in an endoscope by fixing a diffraction grating at a certain distance away from an imaging device.

As for a measurement of deviation, the conventional method has been manual operations by an operator who identifies centers of the spots from the observations of a displayed image and registers positions of the spots on a display by means of a digitizer. It can easily be seen that such operations are extremely cumbersome as well as time consuming.

To alleviate this situation, the measurements of the positions of the centers of the spots can be handled automatically by means of the binarization of a displayed view according to a particular threshold brightness and the thinning of the spot pattern.

However, determining an appropriate threshold brightness can be very subtle, because errors such as false identifications of empty points as spots or misidentifications of spots as empty points due to smearings or noises may easily occur, and even one such error can lead to an incorrect recognition of shapes.

SUMMARY OF THE INVENTION

It is therefore an object of the present invention to provide an endoscope with a device for shape recognition in which measurements of spot positions are automatic, results of spot identification are indicated in a manner that facilitates simple and quick inspections, and errors in the spot identification can be corrected in a simple and quick manner.

This object is achieved in the present invention by providing an endoscope comprising, light source means for generating illumination lights; beam generator means for generating projection lights; a scope including diffraction grating means for producing patterned beams from the projection lights, imaging device means for taking images of objects to be imaged, and light guide means for illuminating the objects by illumination lights; camera control unit means for converting signals from the imaging device means into image signals; display means for displaying images taken; means for identifying positions of the spots made on the objects by means of the patterned beams; means for indicating the positions of the spots identified by the identifying means on the display means; means for correcting errors found in the positions of the spots identified by the identifying means; and means for adjusting the indications on the display means of the positions of the spots by the indicating means according to the corrections made by the correcting means.

Other features and advantages of the present invention will become apparent from the following description taken in conjunction with the accompanying drawings.

DETAILED DESCRIPTION OF THE PREFERRED EMBODIMENTS

Figure 1:
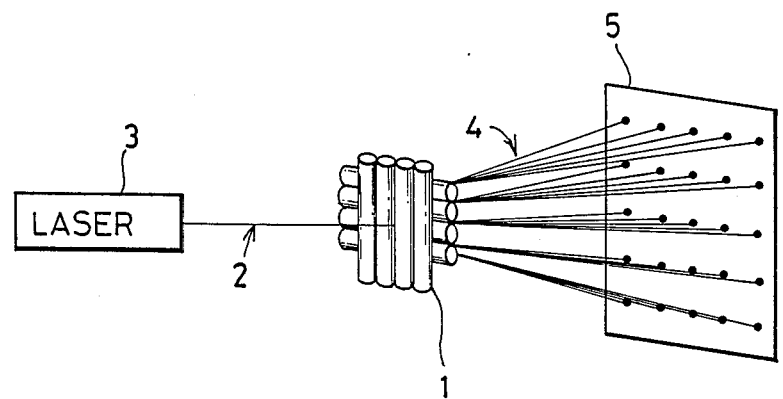
FIG. 1 is an illustration for explaining the manner of producing patterned beams.
Figure 2:
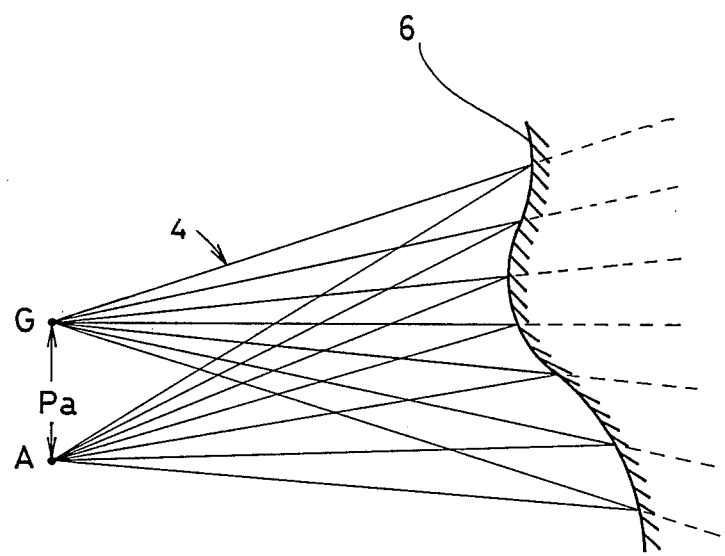
FIG. 2 is an illustration for explaining a phenomenon of parallax.
Figure 3:
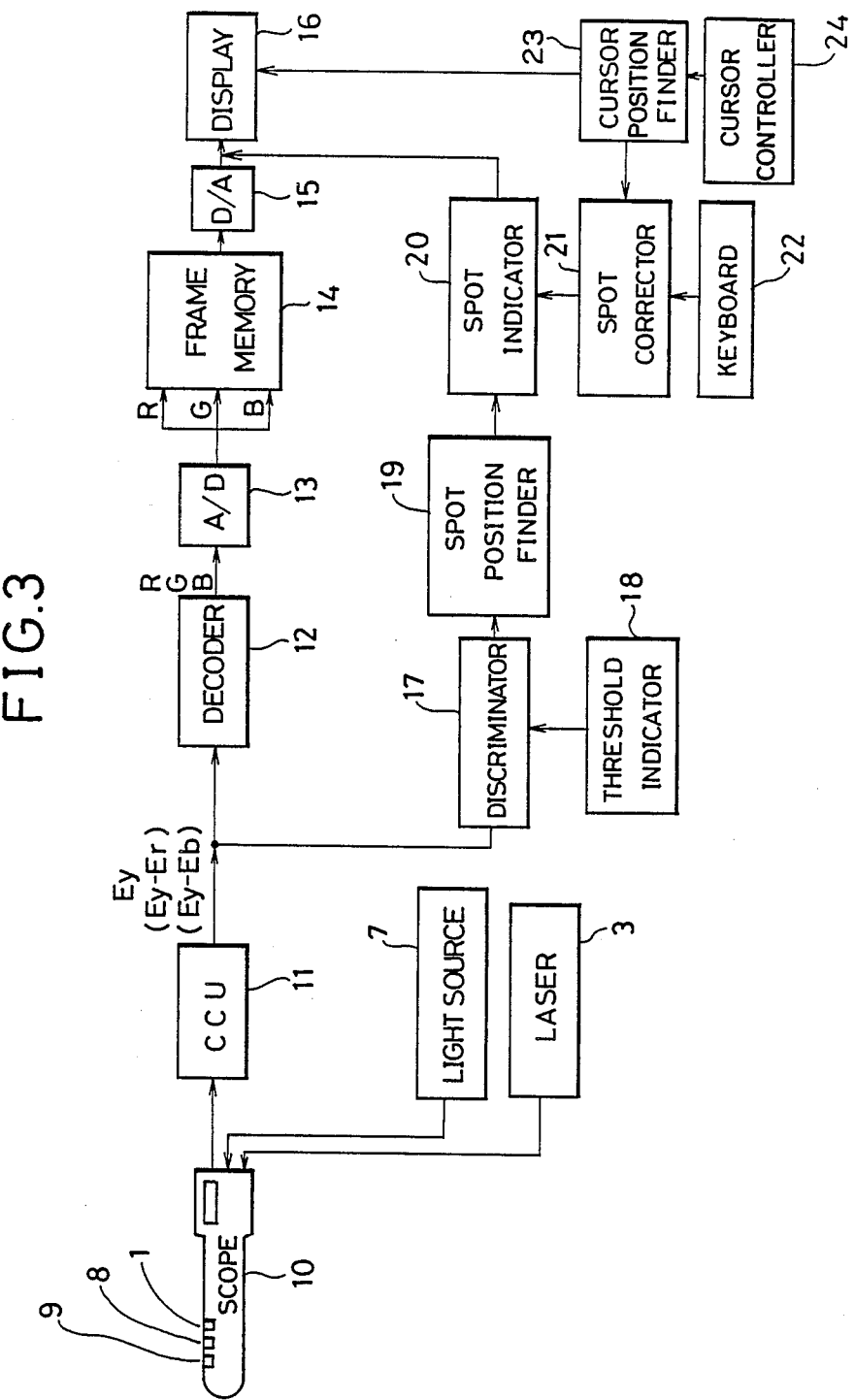
FIG. 3 is a block diagram of one embodiment of an endoscope according to the present invention.
Figure 4:
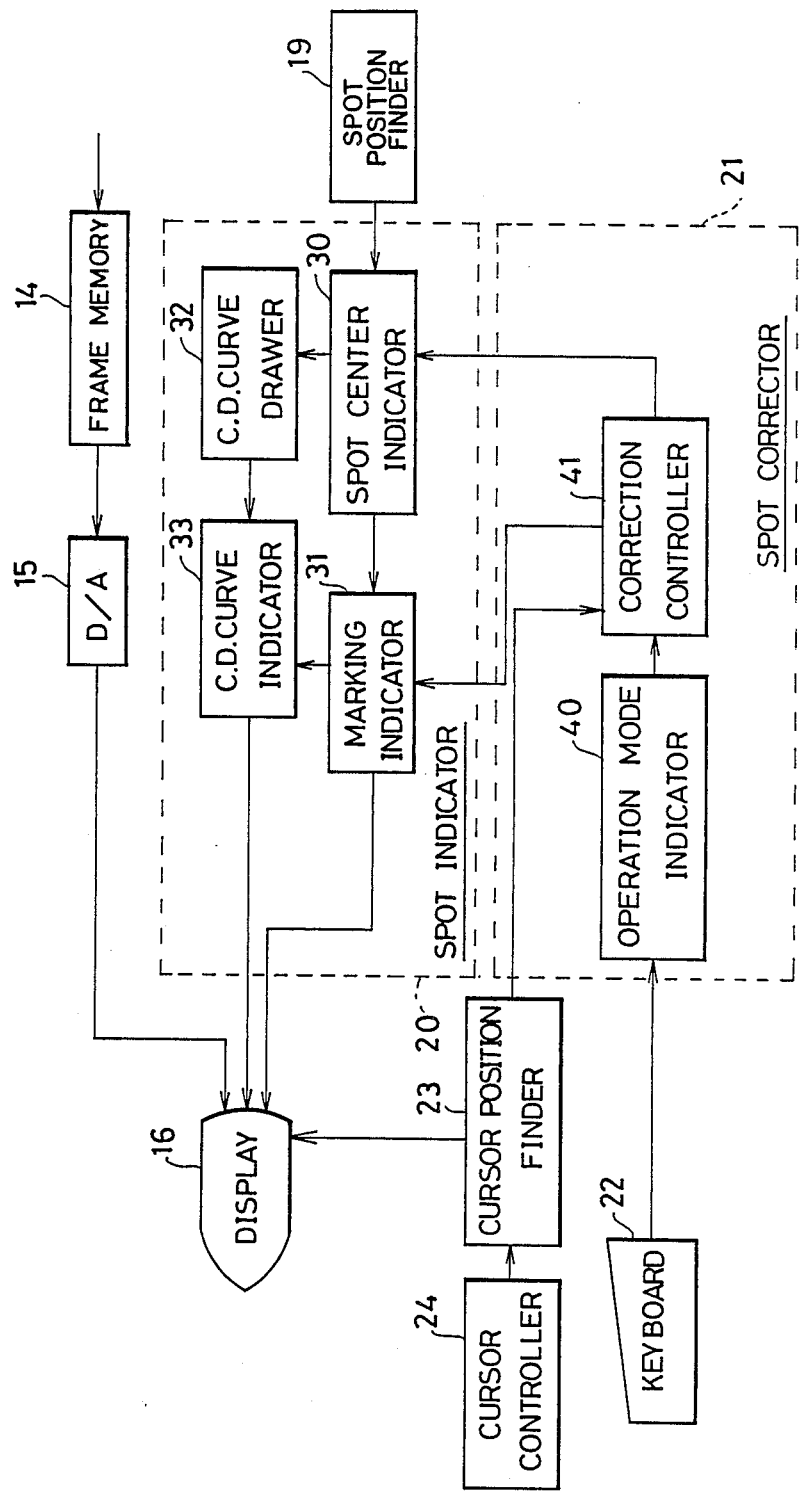
FIG. 4 is a detailed block diagram of an essential part of the endoscope of FIG. 3.

Referring now to FIGS. 3 and 4, there is shown one embodiment of an endoscope according to the present invention.

The endoscope of this embodiment is comprised of a laser 3 for generating projection lights; a light source 7 for generating illumination lights, a scope 10 including a diffraction grating 1 for producing patterned beams, an imaging device 8 for taking images of objects, and a light guide 9 for illustrating objects by the illumination lights; a camera control unit (CCU) 11 for extracting image signals from output signals of the imaging device 5; a decoder 12 for converting image signals into RGB signals; an A/D converter 13; a frame memory 14 for storing image signals; a D/A converter 15; a display 16 for displaying images of the objects; a discriminator 17 for binarizing image signals; a threshold indicator 18 for indicating threshold brightness to the discriminator 17; a spot position finder 19 for thinning the binarized image signals; a spot indicator 20 for indicating positions of spots; a spot corrector 21 for correcting the positions of the spots; a keyboard 22 for selecting a mode of correction; a cursor position finder 23 for indicating coordinates of a cursor on the display 16; and a cursor controller 24 for moving the cursor on the display 16.

The details of the spot indicator 20 and the spot corrector 21 are shown in FIG. 4 where the spot indicator 20 includes a spot center indicator 30 for indicating coordinates of centers of the spots, a marking indicator 31 for attaching markings to the centers of the spots, a common degree (C.D.) curve drawer 32 for determining C.D. curves, and a C.D. curve indicator 33 for indicating C.D. curves, while the spot corrector 21 includes an operation mode indicator 40 for indicating mode of correction selected at the keyboard 22, and a correction controller 41 for making corrections.

Figure 5:
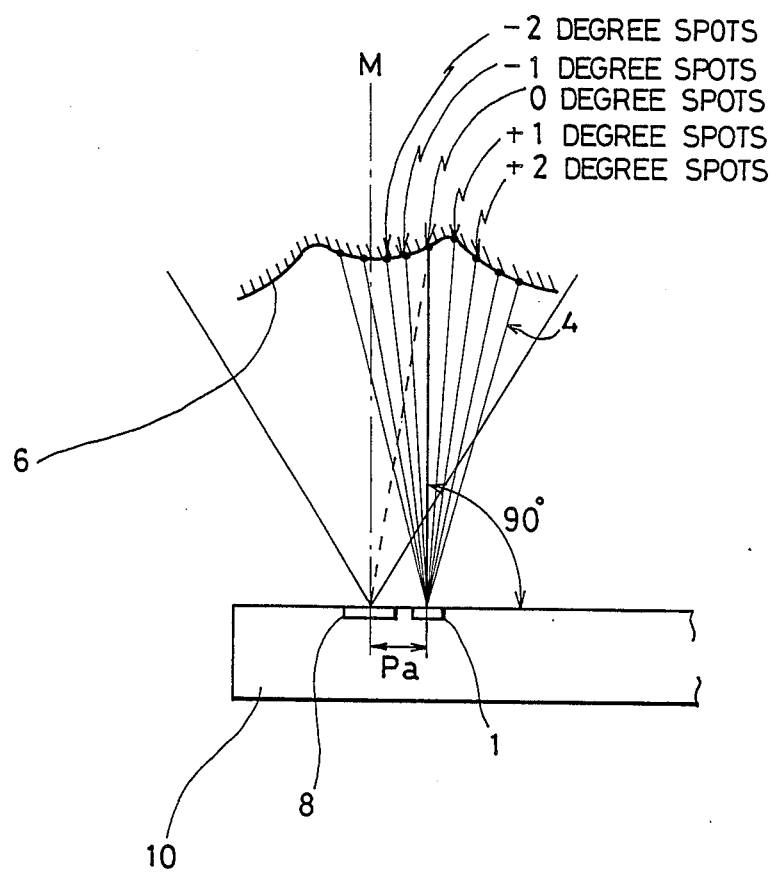
FIGS. 5, 6, and 7 are illustrations for explaining operations of the endoscope of FIG. 3.

A detailed view of the top portion of the endoscope 10 is shown in FIG. 5. As in the prior art, the patterned beams 4 produced from laser beams 2 from the laser 3 by the diffraction grating 1 are projected on the object 6 to be imaged. The diffraction grating 1 is mounted at the distance Pa away from the imaging device 8. A forceps insertion aperture may be utilized as the location to mount the diffraction grating 1. Spots on the object 6 resulting from those beams whose directions make 90° from the direction of the length of the endoscope 10 are called 0 degree spots, as indicated in FIG. 5. Spots adjacent to the right of 0 degree spots are called +1 degree spots, while spots adjacent to the left of 0 degree spots are called −1 degree spots, and so on. The center of the view of the imaging device 8 is indicated by the line labeled as M.

Figure 6:
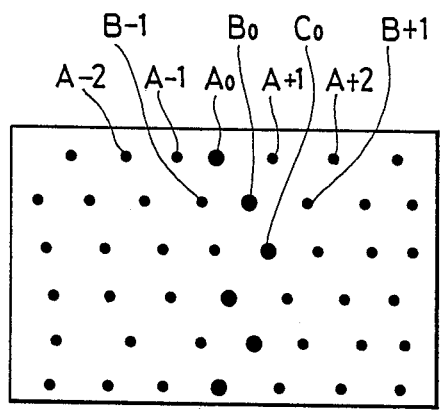

Such spots when viewed from the imaging device 8 at the distance Pa from the diffraction grating 1 appear to be in a pattern deviated from the original pattern of the patterned beams, the deviation reflecting the shape of the object 6, due to parallax. Zn exmaple of an image taken by the imaging device 8 appearing on the display 16 is shown in FIG. 6, where the horizontal direction corresponds to the direction of the length of the endoscope 10, and different letters of labels given to the spots designate rows in the original pattern from which the spots originate while subscripts indicate degrees assigned to the spots which correspond to columns in the original pattern from which the spots originate. Also, the 0 degree spots are shown by dots larger than those for the spots of other degrees to assist recognition. In addition, the spots of the same degree will be joint together by a curve which will be called a common degree (C.D.) curve. It can easily be seen that in this exemplary view, the deviation is only in the horizontal direction.

The system operates as follows. Illumination lights produced by the light source 7 are shone on the object 6 to be imaged from the light guide 9. Meanwhile the laser beams 2 produced by the laser 3 are shone through the diffraction grating 1 to produce the patterned beams 4 which are projected on the object 6. Reflections of these illumination lights and the patterned beams 4 by the object 6 are captured by the imaging device 8 in the form of electric signals. At the CCU 11 these electric signals are converted into image signals representing the tristimulus values Ey, Ey-Er, and Ey-Eb. These image signals on one hand are transmitted to the decoder 12 where they are converted into RGB signals. RGB signals are converted into digital RGB signals at the A/D converter 13, and then stored separately in the frame memory 14. To display images, image signals stored in the frame memory 14 are taken out, through the D/A converter 15 where they are converted into analog signals, to the display 16 where images will be shown for observations.

On the other hand, image signals from the CCU 11 are also transmitted to the discriminator 17 where they are binarized with respect to the brightness according to a particular threshold brightness set by the threshold indicator 18. The binary image signals from the discriminator 17 are subjected to the thinning at the spot position finder 19 in order to identify the positions of the centers of the spots. The coordinates on a view of the display 16 of these identified spot centers are obtained at the spot center indicator 30, on the bases of which a marking X will be marked on each point identified as a spot center by the marking indicator 31, and also common degree curves are determined by the C.D. curve drawer 32 and marked by the C.D. curve indicator 33. These markings and common degree curves are superimposed for the sake of inspection on the view on the display 16 of the imaged object with the spot pattern coming from the frame memory 14 through the D/A converter 15 to the display 16.

Figure 7:
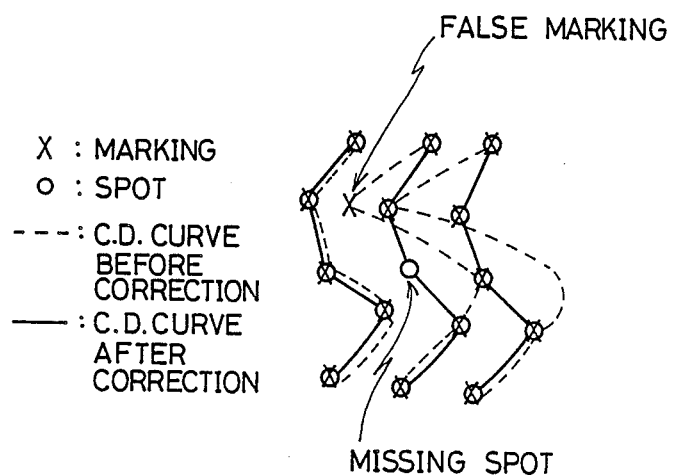

An example of such a view having the markings and the common degree curves superimposed is shown in FIG. 7. In this exemplary view, there is one false marking due to some kind of false identification of an empty point as a spot, and also there is one missing spot due to some kind of misidentification of a spot as an empty point. As a result, the common degree curves shown by dotted lines which are supposed to join the markings corresponding to the spots of the same degree are incorrectly drawn, and the view indicates the shape of the object 6 inaccurately.

When such an error was found upon inspection, the correction can be made by operating the keyboard 22 and the cursor controller 24. At the keyboard 22, whether the desired correction is an insertion or a deletion is specified, while at the cursor controller 24, the cursor on the displayed view is moved to the point where the correction is to be made. The coordinate of the cursor on the displayed view is then obtained by the cursor position finder 23 and then transmitted to the correction controller 41. The choice made at the keyboard 22 is given to the operation mode indicator 40 which identifies the chosen mode and transmit it to the correction controller 41. The correction controller 41 makes the correction of the chosen type at the chosen point to the spot indicator 20 according to the informations given by the cursor position finder 23 and the operation mode indicator 40. The spot indicator 20 then marks corrected markings by the marking indicator 31 and new common degree curves according to these corrected markings by the common curve drawer 32 and the common curve indicator 33, and the corrected view will be shown at the display 16 from which the accurate shape of the object 6 can be recognized.

As described, in this embodiment the shape recognition is facilitated with considerably less demands made upon a user because of the way of displaying identified spots which render the simple and quick inspection possible and the way of correcting any error found upon inspection which render the simple and quick correction possible.

Thus according to the present invention the shape recognition in the endoscope becomes remarkably maneuverable compared with the conventional systems.

It is obvious that many modifications and variations of this embodiment may be made without departing from the novel and advantageous features of the present invention. Accordingly, all such modifications and variations are intended to be included within the scope of the appended claims.

What is claimed is:

1. An endoscope, comprising:
   light source means for generating illumination lights;
   beam generator means for generating projection lights;
   a scope including diffraction grating means for producing patterned beams from the projection lights, imaging device means for taking images of objects to be imaged, and light guide means for illuminating the objects by the illumination lights;
   camera control unit means for converting signals from the imaging device means into image signals;
   display means for displaying images taken;
   means for identifying positions of the spots made on the objects by means of the patterned beams;
   means for indicating the positions of the spots identified by the identifying means on the display means;
   means for correcting errors found in the positions of the spots identified by the identifying means; and
   means for adjusting the indications on the display means of the positions of the spots by the indicating means according to the corrections made by the correcting means.

2. The endoscope of claim 1, wherein the indicating means also indicates curves joining spots related to each other by a particular relationship, and wherein the adjusting means also adjusts these curves indicated by the indicating means.

3. The endoscope of claim 1, wherein the identifying means includes means for binarizing the image taken and means for thinning the binarized image.

* * * * *